United States Patent
Bothe et al.

(10) Patent No.: US 8,087,286 B2
(45) Date of Patent: Jan. 3, 2012

(54) METHOD FOR CHECKING THE PERMEABILITY RATE OF A CLOSED CONTAINER

(75) Inventors: Daniela Bothe, Wallertheim (DE); Hubert Hoelz, Oberheimbach (DE); Christoph Kreher, Ingelheim (DE); Burkhard Metzger, Ingelheim (DE); Christian Scheffler, Ingelheim (DE)

(73) Assignee: Boehringer Ingelheim International, GmbH, Ingelheim am Rhein (DE)

( * ) Notice: Subject to any disclaimer, the term of this patent is extended or adjusted under 35 U.S.C. 154(b) by 726 days.

(21) Appl. No.: 11/996,819

(22) PCT Filed: Jul. 24, 2006

(86) PCT No.: PCT/EP2006/064582
§ 371 (c)(1),
(2), (4) Date: Apr. 17, 2008

(87) PCT Pub. No.: WO2007/012629
PCT Pub. Date: Feb. 1, 2007

(65) Prior Publication Data
US 2008/0295578 A1    Dec. 4, 2008

(30) Foreign Application Priority Data
Jul. 27, 2005   (DE) .......................... 10 2005 035 715

(51) Int. Cl.
*G01M 3/34* (2006.01)
*G01M 3/32* (2006.01)

(52) U.S. Cl. ......................................... 73/49.3; 73/40.7

(58) Field of Classification Search ................. 73/40.7, 73/49.2, 49.3
See application file for complete search history.

(56) References Cited

U.S. PATENT DOCUMENTS

| | | | |
|---|---|---|---|
| 5,316,135 A | 5/1994 | Kneer et al. | |
| 5,553,483 A | 9/1996 | Armentrout et al. | |
| 5,833,088 A | 11/1998 | Kladders et al. | |
| 6,640,615 B1 | 11/2003 | Morrow | |
| 7,017,391 B2 * | 3/2006 | Klein et al. | 73/40.7 |
| 2004/0003653 A1 | 1/2004 | Avila | |

FOREIGN PATENT DOCUMENTS

| | | |
|---|---|---|
| CA | 2 232 151 C | 4/1997 |
| CA | 2 251 828 C | 10/1997 |
| CA | 2 286 759 A1 | 10/1998 |
| CA | 2 319 834 A1 | 9/1999 |
| CA | 2345675 A1 | 4/2000 |

(Continued)

OTHER PUBLICATIONS

Abstract in English for JP2005-009967, Jan. 13, 2005, Applicant: Horiba, Ltd.*

(Continued)

*Primary Examiner* — John Fitzgerald
(74) *Attorney, Agent, or Firm* — Michael P. Morris; David L. Kershner (57) ABSTRACT

In a method for checking the permeability rate of a closed container (3) with respect to a medium, in particular for checking the permeability rate of a film-type container for accommodating a film container for accommodating a pharmaceutical active constituent formulation, the container (3) is filled with a medium, charged with a gas, and the increase in the amount of medium in the gas is then analysed.

25 Claims, 3 Drawing Sheets

FOREIGN PATENT DOCUMENTS

| | | |
|---|---|---|
| CA | 2 348 403 A1 | 5/2000 |
| CA | 2 362 243 A1 | 8/2000 |
| CA | 2 403 148 A1 | 10/2001 |
| CA | 2 499 106 A1 | 4/2004 |
| DE | 102 43 255 A1 | 3/2004 |
| EP | 0 351 137 A2 | 1/1990 |
| EP | 0 532 873 A1 | 3/1992 |
| EP | 1 202 042 A2 | 5/2002 |
| EP | 1 522 838 A2 | 4/2005 |
| GB | 2 376 748 A | 12/2002 |
| JP | 62-56831 | 3/1987 |
| JP | 2005-9967 | 1/2005 |
| WO | 91/14468 A1 | 10/1991 |
| WO | 95/00827 A1 | 1/1995 |
| WO | 96/06011 A2 | 2/1996 |
| WO | 97/12687 A1 | 4/1997 |
| WO | 97/39831 A1 | 10/1997 |
| WO | 98/46522 A1 | 10/1998 |
| WO | 99/43571 A1 | 9/1999 |
| WO | 99/46572 A1 | 9/1999 |
| WO | 00/23037 A1 | 4/2000 |
| WO | 00/27543 A1 | 5/2000 |
| WO | 00/49988 A2 | 8/2000 |
| WO | 01/76849 A1 | 10/2001 |
| WO | 2004/034009 A1 | 4/2004 |

OTHER PUBLICATIONS

International Search Report for PCT/EP2006/064582 mailed Oct. 17, 2006.

Abstract in English for JP62-056831, Mar. 12, 1987, Applicant: Shinkosumosu Denki KK.

* cited by examiner

METHOD FOR CHECKING THE PERMEABILITY RATE OF A CLOSED CONTAINER

BACKGROUND OF THE INVENTION

1. Field of the Invention

The present invention relates to a method for checking the permeability rate of a closed container with respect to a medium, in particular for checking the permeability rate of a film-type container for accommodating a pharmaceutical active constituent formulation.

2. Description of the Related Art

The containers serve inter alia to protect pharmaceutical active constituent formulations against outside environmental influences which, depending on the circumstances, may affect the pharmaceutical quality of the active constituent formulation, wherein in particular moisture penetrating the containers can adversely affect the active constituent formulation. In addition it is necessary in the case of the containers to prevent the permeability of volatile substances of the active constituent formulations during their storage, in order thereby to counteract any change in the pharmaceutical active constituent formulation.

The containers are in particular primary packagings for pharmaceutical active constituent formulations, such as glass, metal, plastics containers and the like. For packaging tablets, capsules, powders and the like, containers designed as film-type containers, so-called blisters, are used, which as a rule consist of a cover film and a carrier film, one or more cups or wells for receiving the active constituent formulation, tablets or capsules being formed in the carrier film. The cover film and the carrier film may be composed of one or more layers of different or identical materials. The cover film is hermetically connected to the carrier film, e.g. by bonding, welding or sealing. Mechanically intact blisters protect an active constituent formulation embedded therein against the entry or influx of substances. Thus, depending on the material, moisture for example can pass through the upper side of the blister, the lower side or through the edges, into the interior.

Liquid active constituent formulations may be packaged in the aforementioned containers as well as in cartridges, which are used for example as active constituent reservoirs for pharmaceutical liquids in inhalers. Such cartridges are known for example from EP 0 532 873, WO 96/06011, WO 97/39831, WO 00/23037, WO 00/27543, WO 00/049988, WO 01/76849, WO 99/43571 or WO 98/46522. A cartridge may for example be used in an inhaler described in WO 97/12687 or WO 91/14468, with which liquid inhalation formulations may be administered by means of specific water-based or alcohol-based formulations free of propellant gas.

In order to be able to determine the hermeticity of the containers, whether as regards liquids or gases penetrating from the outside, e.g. moisture in the form of water or water vapour, or liquids or gases exiting from the inside, various methods are known from the prior art. This applies in particular to blisters. For example, a container filled with a desiccant is exposed to specific environmental conditions (e.g. 40° C., 75% atmospheric humidity) and is then checked as regards hermeticity via the weight increase of the container over time. Such a method often takes months in order to detect low leakage rates. In a further method a container is sealed, e.g. under a helium atmosphere, helium thereby being trapped in the container. The container is then tested for outflowing helium. In this connection the container may be placed in a measurement chamber, gas exiting from the container being detected with suitable measurement systems connected to the measurement chamber. In this method it is necessary to establish a constantly uniform high helium concentration in the container in order to obtain reproducible results, which is not always easy to realise in a production process. In a further method the container prepared under normal conditions is enclosed in a pressure-stable test chamber that is filled with gas. Carbon dioxide, helium or krypton is normally used as gas. After a certain time the container being investigated is removed from the test chamber and tested for exiting gas. Alternatively the container can be placed in a measurement chamber, following which gas exiting from the container can be detected with suitable measurement systems in the measurement chamber. The applicability of these methods is restricted by the detection limit of the gas in the measurement chamber, since in the case of a per se fluid-type container, in both methods only relatively little gas (ppm range) can penetrate the container and accordingly only very little gas can pass from the container into the measurement chamber.

From WO 2004/034 009 a method is known for testing the hermeticity of closed containers that contain a pharmaceutical active constituent formulation in a chamber provided for this purpose in their interior. A sealed film-type container is charged with a first gas, which differs from a second gas enclosed in the container in that the increase of the first gas in the interior of the container can be analysed. After opening the container and removing part of the gas that is contained in the interior of the chamber for the active constituent formulation, a qualitative and/or quantitative analysis of the removed gas is carried out.

SUMMARY OF THE INVENTION

The object of the invention is to provide an improved method of the type mentioned in the introduction that provides data on the hermeticity of the container rapidly and in situ during production.

According to the invention this object is achieved by filling the container with the medium, charging the container with a gas, and then analysing the increase in the amount of the medium in the gas.

The method is based on the idea that for a given drop in partial pressure the direction of the permeability or permeation plays no role in the samples to be investigated. In other words, it is assumed that the permeability from the outside to the inside and from the inside to the outside are the same. By suitable analysis methods the medium can be detected in very minor amounts in the ppb range within the gas already after a relatively short time, whereby a rapid process procedure is ensured.

A liquid is preferably used as medium. Since a relative humidity of 100% exists within the container, a permeation of the liquid from the inside to the outside takes place and the gas charging the container absorbs the exiting vapour, the amount of which can be determined by subsequent analysis of the gas. Obviously the medium in the gas can also be analysed in the case where the container has a leak through which a relatively large amount of liquid escapes. A gaseous medium, preferably water vapour, may also be used as medium.

In order to protect the container against deformation as well as damage due to the charging with the gas, the liquid is absorbed by a porous solid body that matches the shape and size of the container interior. Conveniently the solid body is made of clay. Clay is a material that is relatively easy to process, and that can absorb a relatively large amount of liquid. The clay solid body is calcined before use, in particular in a spray calcining method at ca. 1000° C.

Water is preferably used as the liquid. Water is harmless to handle and can be detected even in very small amounts in a large number of gases, in particular noble gases. The gas that is used should obviously be such that an absorption of water in the gas can be quantitatively determined.

Conveniently the calcined clay is impregnated with water, the clay body prepared in this way completely filling the interior of the container. The container is for example a blister with a plurality of cups, the clay body being placed in each cup and the cups then being tightly sealed. The blister is next charged with the gas. If the container is not gas tight or the material is permeable to water vapour, the water vapour escapes from the interior of the container into the gas. After a certain time a stationary state is reached as regards the permeability rate of the water vapour. This steady state permeability rate then results in an increase of the water vapour in the gas, which can be measured. In this way the release of water vapour can be calculated for an individual cup, assuming that all cups, i.e. all individual cavities, have been equally well prepared.

Nitrogen is preferably used as gas. Conveniently the gas is dried, or its water content is determined, before the medium is charged with the gas. The container thus ideally exists in an external environment containing almost 0% moisture or a known moisture content, and the gas entrains moisture exiting from the container, whereby an increase of moisture can be established relatively easily.

To pressurise the container the container is advantageously placed in a sealed test chamber through which the gas flows. In order to reduce as far as possible influences of the ambient temperature on the outflow of the medium, the test chamber is designed so that it can be climatically controlled. On account of the climatisation of the test chamber with a heating/cooling medium at a constant temperature, fluctuations in the measurement values due to the temperature can be prevented. In this connection a temperature is adjusted that prevails for example in specific climatic zones. The method is therefore preferably carried out at a temperature between 0° C. and 50° C., in particular between 10° C. and 30° C., and preferably at room temperature.

So that the permeability rate of the medium adopts a stationary state after as short a time as possible, according to a modification of the invention the seals of the test chamber are dried beforehand.

In order to obtain analysis and measurement results that are as accurate and reproducible as possible, the gas preferably flows through the test chamber at a constant mass flow and at a constant pressure.

In order to reduce the time required to reach the stationary state reflecting the permeability of the water vapour, the container is preferably dried first before being placed in the test chamber. This preliminary drying reduces, especially in the case of blisters, mainly the amounts of water that are stored in the outerlying layers. Thanks to the preliminary drying of the container the overall measurement time can be reduced for example to 180 hours, whereas the measurement time in a non-pre-dried container is for example 250 hours.

So that as little moisture as possible reaches the test chamber when the containers are placed therein and so that environmental influences are largely reduced, the test chamber is conveniently placed in a closed chamber. The closed chamber includes a glove box facility so that manipulations can be carried out in the interior of the chamber.

According to a further modification an evaluation unit that comprises quartz resonators is used to analyse the gas. Such quartz resonators known to the person skilled in the art serve to detect traces of moisture in gases in the ppm/ppb range and have an extremely rapid response, whereby highly accurate measurements are possible. The quartz resonator is provided with a hygroscopic layer that is selective for water molecules and that has a high affinity for removing water molecules from the measurement gas. Obviously a computing unit with at least one storage module and a display device is furthermore associated with the evaluation unit, in order to evaluate, store and display the measurement results obtained by means of the quartz resonators.

A preferred container for use in the method discussed hereinbefore is a blister for medicaments. The blister consists of at least one cover film and at least one cup for the carrier film accommodating the active constituent formulation, wherein the cover film and the carrier film are tightly joined together in order to seal the cup hermetically. If the same materials are used for the cover film and the carrier film, then the permeability-dependent properties of the materials can be determined in comparison tests, whereby important knowledge can be derived for the development and improvement of blisters. Conveniently the cover film is joined to the carrier film by means of a hot sealing lacquer. The determination of the permeability rate of the hot sealing lacquer layer shows that this layer is responsible for a significant proportion of the permeability rate of the whole blister. This means for the optimisation of a blister that a change of the thickness of the hot sealing lacquer or of its properties has a greater effect as regards the water vapour permeability than a change of the properties of the cover film and/or carrier film. In an optimised blister an amount of for example between 2 and 10 $g/m^2$, preferably between 4 and 7 $g/m^2$, more preferably 5.5 $g/m^2$ of hot sealing lacquer is applied. In this connection the thickness of the hot sealing lacquer is for example between 2.5 and 8.5 µm, preferably between 4.5 and 6.5 µm, and most preferably 5.5 µm.

In their configuration the cover film and/or the carrier film are formed as metal and/or plastics and/or paper films. These materials may be present in several layers. Typical metal films (foils) include for example aluminium films and aluminium composite films that are formed from aluminium and for example a plastics. As material for the plastics films there may be used polyvinyl chloride (PVC), cycloolefin copolymer (COC), polychlortrifluoroethylene (PCFE), polyethylene (PE), polypropylene (PP), polyethylene terephthalate (PET), polycarbonate (PC), polyester (UP), polyacrylate, polyamide (PA) or other plastics. A blister often consists of a cover film of aluminium that seals the carrier film for receiving the pharmaceutical product or active constituent. This thermoformed carrier film may likewise comprise an aluminium film in order to prevent the entry of water into the cup that accommodates the pharmaceutical product. In order to create a further diffusion barrier and to increase the mechanical stability of the blister, optionally at least the aluminium film of the carrier film may be covered on one or both sides with further plastics and/or paper films.

A further container for use in the method mentioned above is a closed double-layer bottle-shaped container with a rigid outer casing and an inner container that is mechanically joined only in a punctiform manner to the outer casing and that can collapse with respect to the outer container. Preferably the container is produced by means of a co-extrusion process. Conveniently the outer container consists of polypropylene and the inner container of polyethylene. The outer container contains at least one valve opening that enables air to flow in between the outer container and the inner contain. The inner container is similar to a plastics bag and can contract and collapse when, from the closed system under pressure, a liquid is withdrawn from the inner container. Details of the container closed with a cap are described for example in WO 96/06011. The container serves to accommodate a liquid pharmaceutical formulation and is used as a cartridge in propellant-free inhalers. The liquid formulations are preferably solutions where water is the main constituent of the solvent.

In addition, for use in the method described above the container is a sealed collapsible bag provided with a flange. Conveniently the bag consists of a metal film, such as for example an aluminium film and/or a plastics film, or a metal film coated with a plastics. Preferably the bag is embedded in a metal or plastics sleeve. Such a container serves as a cartridge for propellant-free nebulisers and is disclosed in WO 99/43571.

In principle any type of formulations are suitable as medicament formulations for the containers that can be tested by the method according to the invention. Preferably containers with medicaments for inhalative application are tested.

Particularly preferred in this connection are medicaments that are selected from the group consisting of anticholinergic agents, betamimetics, steroids, phosphodiesterase IV inhibitors, LTD4 antagonists and EGFR kinase inhibitors, antiallergic agents, ergot alkaloid derivatives, triptanes, CGRP antagonists, phosphodiesterase V inhibitors, as well as combinations of such active substances, e.g. betamimetics plus anticholinergic agents or betamimetics plus antiallergic agents. In the case of combinations at least one of the active constituents contains preferably chemically bound water. Anticholinergic agent-containing active substances are preferably used, as single preparations or in the form of combination preparations.

The following in particular may be mentioned as examples of effective constituents or their salts:

Anticholinergic agents are preferably selected from the group consisting of tiotropium bromide, oxitropium bromide, flutropium bromide, ipratropium bromide, glycopyrronium salts, trospium chloride, tolterodine, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide, tropenol 9-hydroxy-fluorene-9-carboxylate methobromide, tropenol 9-fluoro-fluorene-9-carboxylate methobromide, scopine 9-hydroxy-fluorene-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, cyclopropyltropine methyl 4,4'-difluorobenzilate methobromide, tropenol 9-hydroxy-xanthene-9-carboxylate methobromide, scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide and scopine 9-hydroxymethyl-xanthene-9-carboxylate methobromide, optionally in the form of their racemates, enantiomers or diastereomers, and optionally in the form of their solvates and/or hydrates.

Betamimetics which may be used are preferably selected from the group consisting of albuterol, bambuterol, bitolterol, broxaterol, carbuterol, clenbuterol, fenoterol, formoterol, hexoprenaline, ibuterol, indacaterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenot, sulphonterol, tiaramide, terbutaline, tolubuterol, CHF-1035, HOKU-81, KUL-1248, 3-(4-{6-[2-hydroxy-2-(4-hydroxy-3-hydroxymethylphenyl)-ethylamino]-hexyloxy}-butyl)-benzolsulphonamide, 5-[2-(5,6-diethyl-indan-2-ylamino)-1-hydroxyethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1.4-benzoxazin-8-yl]-2-[3-(4-n-butyloxyphenyl)-2-methyl-2-propylamino]ethanol, 1-[2H-5-hydroxy-3-oxo-4H-1.4-benzoxazin-8-yl]-2-{4-[3-(4-methoxyphenyl)-1.2.4-triazol-3-yl]-2-methyl-2-butylamino}ethanol, 5-hydroxy-8-(1-hydroxy-2-isopropylaminobutyl)-2H-1.4-benzoxazin-3-(4H)-one, 1-(4-amino-3-chloro-5-trifluormethylphenyl)-2-tert.-butylamino) ethanol and 1-(4-ethoxycarbonylamino-3-cyano-5-fluorophenyl)-2-(tert.-butylamino)ethanol, optionally in the form of their racemates, enantiomers or diastereomers, and optionally in the form of their pharmacologically acceptable acid addition salts, solvates and/or hydrates.

Steroids which may be used are preferably selected from the group consisting of prednisolone, prednisone, butixocortpropionate, RPR-106541, flunisolide, beclomethasone, triamcinolone, budesonide, fluticasone, mometasone, ciclesonide, rofleponide, ST-126, dexamethasone, (S)-fluoromethyl 6α,9α-difluoro-17α-[(2-furanylcarbonyl)oxy]-11β-hydroxy-16α-methyl-3-oxo-androsta-1,4-diene-17β-carbothionate, (S)-(2-oxo-tetrahydro-furan-3S-yl) 6α,9α-difluoro-11β-hydroxy-16α-methyl-3-oxo-17α-propionyloxy-androsta-1,4-diene-17β-carbothionate and etiprednol-dichloroacetate (BNP-166), optionally in the form of their racemates, enantiomers or diastereomers, and optionally in the form of their salts and derivatives, their solvates and/or hydrates. PDE IV-inhibitors which may be used are preferably selected from the group consisting of enprofyllin, theophyllin, roflumilast, ariflo (cilomilast), CP-325,366, BY343, D-4396 (Sch-351591), AWD-12-281 (GW-842470), N-(3,5-dichloro-1-oxo-pyridin-4-yl)-4-difluoromethoxy-3-cyclopropylmethoxybenzamide, NCS-613, pumafentine, (−)$_p$-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyanoS-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl) cyclohexan-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]

acetate, (S)-(−)-ethyl[4-(3-cyclopentyloxy-4-methoxyphenyl)pyrrolidin-2-ylidene]acetate, CDP840, Bay-198004, D-4418, PD-168787, T-440, T-2585, arofyllin, atizoram, V-11294A, CI-1018, CDC-801, CDC-3052, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of their racemates, enantiomers or diastereomers, and optionally in the form of their pharmacologically acceptable acid addition salts, solvates and/or hydrates.

LTD4-antagonists which may be used are preferably selected from the group consisting of montelukast, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3 (3-(2-(2,3-dichlorothieno[3,2-b]pyridin-5-yl)-(E)-ethenyl)phenyl)-3-(2-(1-hydroxy-1-methylethyl) phenyl)propyl)thio)methyl)cyclopropane-acetic acid, pranlukast, zafirlukast, [2-[[2-(4-tert-butyl-2-thiazolyl)-5-benzofuranyl]oxymethyl]phenyl]acetic acid, MCC-847 (ZD-3523), MN-001, MEN-91507 (LM-1507), VUF-5078, VUF-K-8707 and L-733321, optionally in the form of their racemates, enantiomers or diastereomers, optionally in the form of their pharmacologically acceptable acid addition salts, and optionally in the form of their salts and derivatives, their solvates and/or hydrates.

EGFR-kinase inhibitors which may be used are preferably selected from the group consisting of cetuximab, trastuzumab, ABX-EGF, Mab ICR-62, 4-[(3-chloro-4-fluorophenyl)amino]-6-{4-(morpholin-4-yl)-1-oxo-2-buten-1-yl]amino}-7-cyclopropylmethoxy-quinazoline, 4-[(R)(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)ethoxy]-7-methoxy-quinazoline, 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-ethynylphenyl)amino]-6,7-bis-(2-methoxy-ethoxy)-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynylphenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluorophenyl)amino]-6-{1-[(piperidin-1-yl)carbonyl]-piperidin-4-yloxy}-7-methoxy-quinazoline, 4-[(3-chloro-4-fluoro-phenyl)amino]-6-(cis-4-{N-[(morpholin-4-yl)carbonyl]-N-methylamino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy]-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynylphenyl)amino]-6-(1-acetyl-piperidin-4-yloxy)-7-methoxy-quinazoline, 4-[(3-ethynylphenyl)amino]-6-(1-methyl-piperidin-4-yloxy)-7-methoxy-quinazoline, 4-[(3-ethynylphenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy) quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)-amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluorophenyl)-amino]-6-(trans-4-{N-[(morpholin-4-yl)carbonyl]-N-methyl-amino}-cyclohexan-1-yloxy)-7-methoxy-quinazoline, 4-[(3-chloro-4-fluorophenyl)-amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluorophenyl)-amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxy-ethyl)carbonyl]-piperidin-4-yloxy}-7-methoxy-quinazoline, optionally in the form of their racemates, enantiomers or diastereomers, and optionally in the form of their pharmacologically acceptable acid addition salts, their solvates and/or hydrates.

Acid addition salts with pharmacologically acceptable acids that the compounds are capable of forming are understood to mean for example salts selected from the group consisting of hydrochloride, hydrobromide, hydriodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of antiallergics are: disodium cromoglycate, nedocromil.

Examples of derivatives of the ergot alkaloids are: dihydroergotamine, ergotamine.

For inhalation it is possible to use medicaments, medicament formulations and mixtures including the abovementioned active constituents, as well as their salts, esters and combinations of these active constituents, salts, addition products and esters.

The method according to the invention is preferably used for containers for the aforementioned active constituents or combinations, but is however not restricted to the aforementioned active constituents.

It is understood that the aforementioned features and those still to be explained may be used not only in the respective given combination, but also in other combinations. The scope of the invention is defined only by the claims.

DESCRIPTION OF THE FIGURES

The invention is described in more detail hereinafter with the aid of an embodiment and with reference to the accompanying drawings, in which.

DETAILED DESCRIPTION OF THE INVENTION

Figure 1:
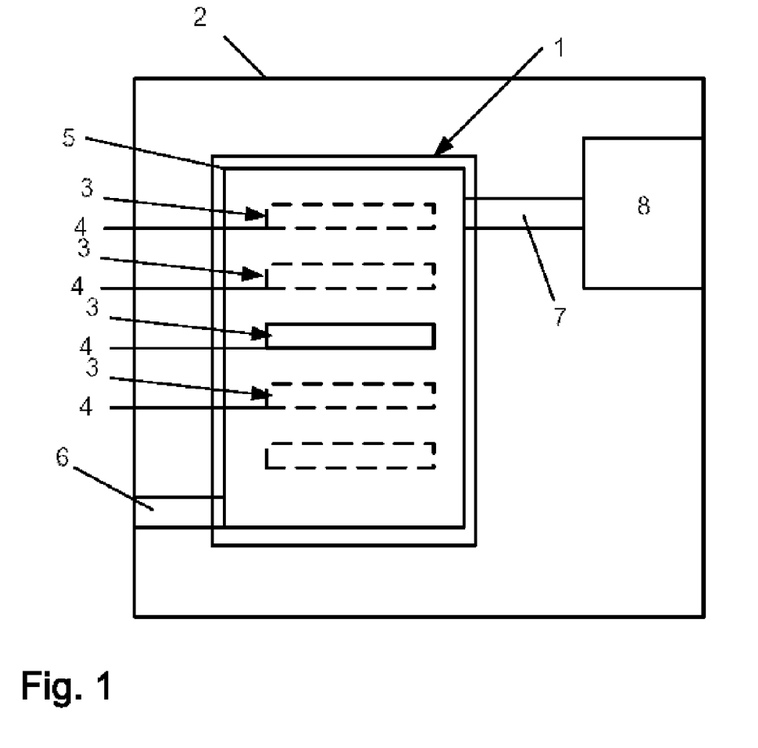
FIG. 1 is a diagrammatic representation of an arrangement for carrying out the method according to the invention.
Figure 2:
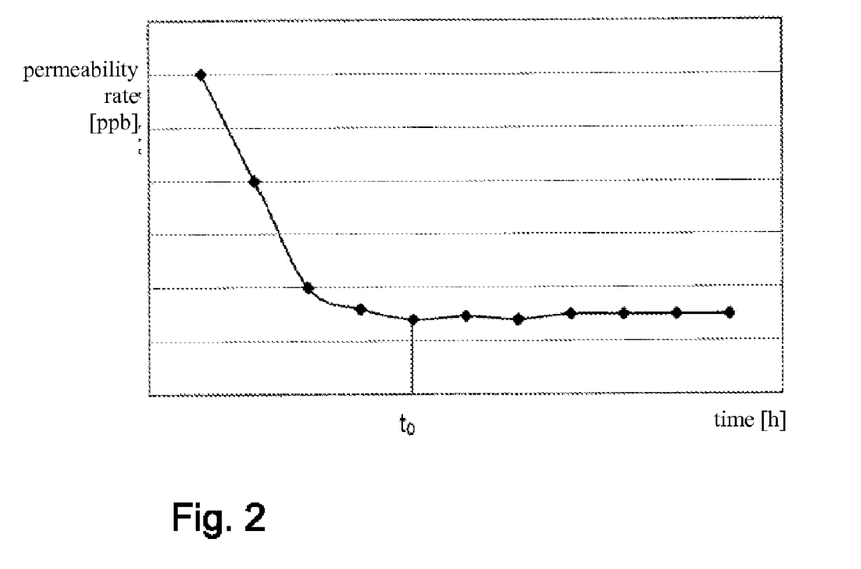
FIG. 2 is a diagram illustrating the permeability rate over time during the implementation of the method.

In order to carry out the method a closed sample chamber 1 with pre-dried seals is inserted in a similarly closed chamber 2. One or more containers 3, which in the present case are configured as blisters 4 whose permeability behaviour is to be checked, are arranged in the sample chamber 1. In order to accelerate the method the blisters 4 are dried first before being placed in the sample chamber 1. In order to produce a constant temperature the sample chamber 1 is climatically controlled by passing a heating/cooling medium at constant temperature through its outer double jacket 5. The sample chamber 1 has an inlet 6 and an outlet 7 for a pre-dried gas, the outlet 7 being coupled to an evaluation unit 8 comprising a quartz resonator for the analysis of the gas. Solid clay bodies 10 are placed in the cups 9 of the blisters 4 for accommodating a pharmaceutical active constituent formulation, which solid bodies are soaked in water and completely fill the cup 9, in order to avoid the cup being mechanically damaged due to the charging with the gas; nitrogen is used as gas. The permeability rate of the blister 4 for water vapour is measured by the method using a calibration model, the method being based on the consideration that for a given partial pressure drop the direction of the permeability in the blisters 4 to be investigated plays no rôle. It is therefore assumed that the permeability or permeation from the outside to the inside behaves exactly the same as from the inside to the outside. Water vapour escapes outwardly from the tightly closed blister 4, the cups 9 of which contain the solid bodies 10 soaked with water, since a relative humidity of 100% prevails inside the cups 9, while the dried nitrogen with a minimal residual moisture content flows through the blister 4. The nitrogen absorbs the water vapour exiting from the cups 9 of the blister 4 and transports it to the evaluation unit 8. The mass throughflow and the pressure of the nitrogen as well as the temperature of the sample chamber 1 are maintained constant so that precise reproducible measurement results can be obtained. The quartz resonators of the evaluation unit 8 serve to determine the moisture content in the nitrogen and operate in a measurement range of greater than zero ppb. Due to the rapid response of the quartz resonators a quasi-continuous measurement of the moisture, i.e. of the increase in the amount of water in the nitrogen, is possible. During the process a stationary state of the water vapour concentration is established after a time $t_o$, which reflects the permeability of the water vapour. If the residual moisture content of the nitrogen is subtracted from this value, the permeability rate is obtained for the number of cups 9 of the blister 4 within the sample chamber 1. Assuming that all cups 9 and blisters 4 have been processed and prepared equally well, the release of water vapour from a cup 9 can be calculated from the permeability rate at time $t_0$, which is of particular significance in developing containers 3, in particular blisters 4, for protecting the pharmaceutical active substance formulation contained therein. In the same way blisters 4 from a continuous production run can be checked as regards their hermeticity on the basis of the permeability rate. On account of the preliminary drying of the blisters 4 as well as the seals of the sample chamber 1, the stationary state of the permeability rate is reached relatively early, which means that the method can be carried out relatively quickly.

Figure 3:
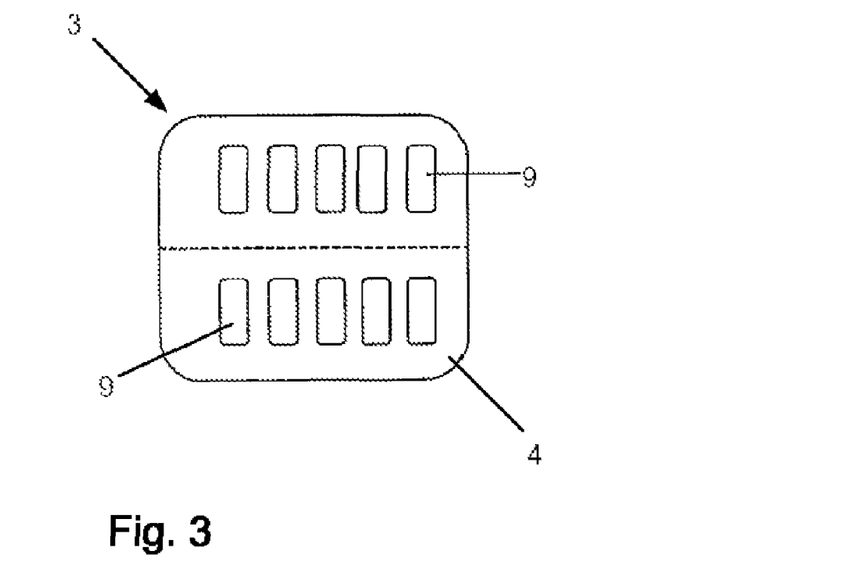
FIG. 3 is a diagrammatic plan view of a container configured as a blister for use in the method according to the invention.
Figure 4:
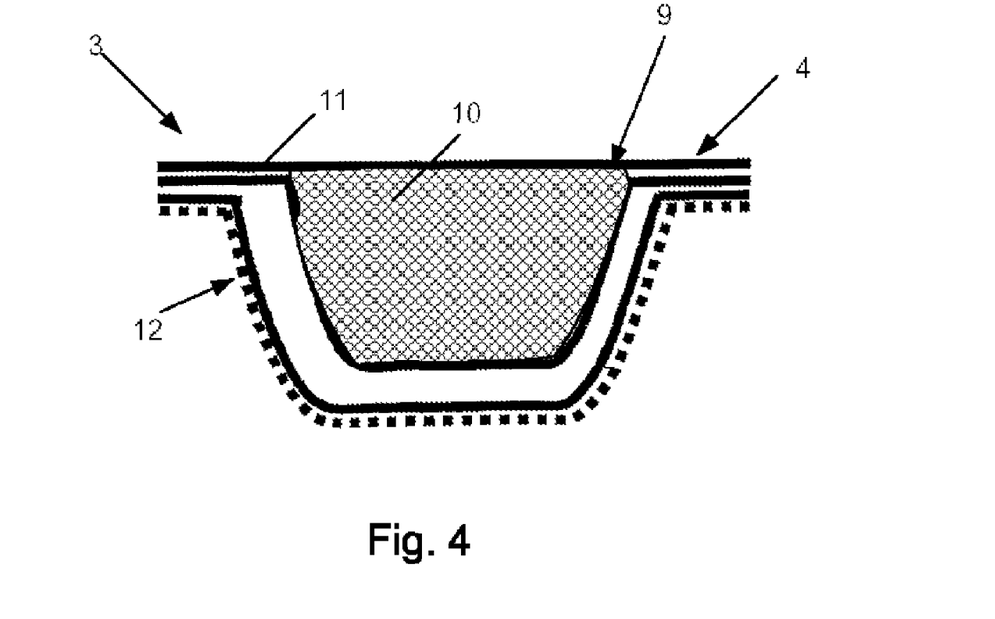
FIG. 4 is a partial section through the blister according to FIG. 3.

Blisters 4 with the following layer sequence are provided for use in the method. A cover film 11 is produced from aluminium and has a thickness of 10 to 80 μm, preferably 20 to 50 μm, in particular 30 to 40 μm. The cover film 11 is hermetically joined by means of a hot sealing lacquer to a thermoformed carrier film 12 containing the cups 9. The carrier film 12 consists on the product-contacting side of a PVC, PP, PE layer or the like with a thickness between 10 and 200 μm, preferably between 15 and 50 μm, in particular between 20 and 40 μm. This film is joined to an aluminium film whose thickness is preferably 30 to 60 μm, advantageously 35 to 50 μm. A polyamide film that has a thickness between 10 and 40 μm, preferably 15 to 30 μm, adjoins the aluminium film. In an alternative carrier film 12 the PVC film on the side facing the product is replaced by a polypropylene film or the like.

In the most particularly preferred blister 4 the cover film 11 consists of a 38 μm-thick aluminium film and the hot sealing lacquer. The carrier film 12 on the side facing the pharmaceutical product is produced from a 30 μm-thick PVC film, a 45 μm-thick aluminium film adjoining the latter, as well as a 20 μm-thick polyamide film on the outside.

Figures 5, 6:
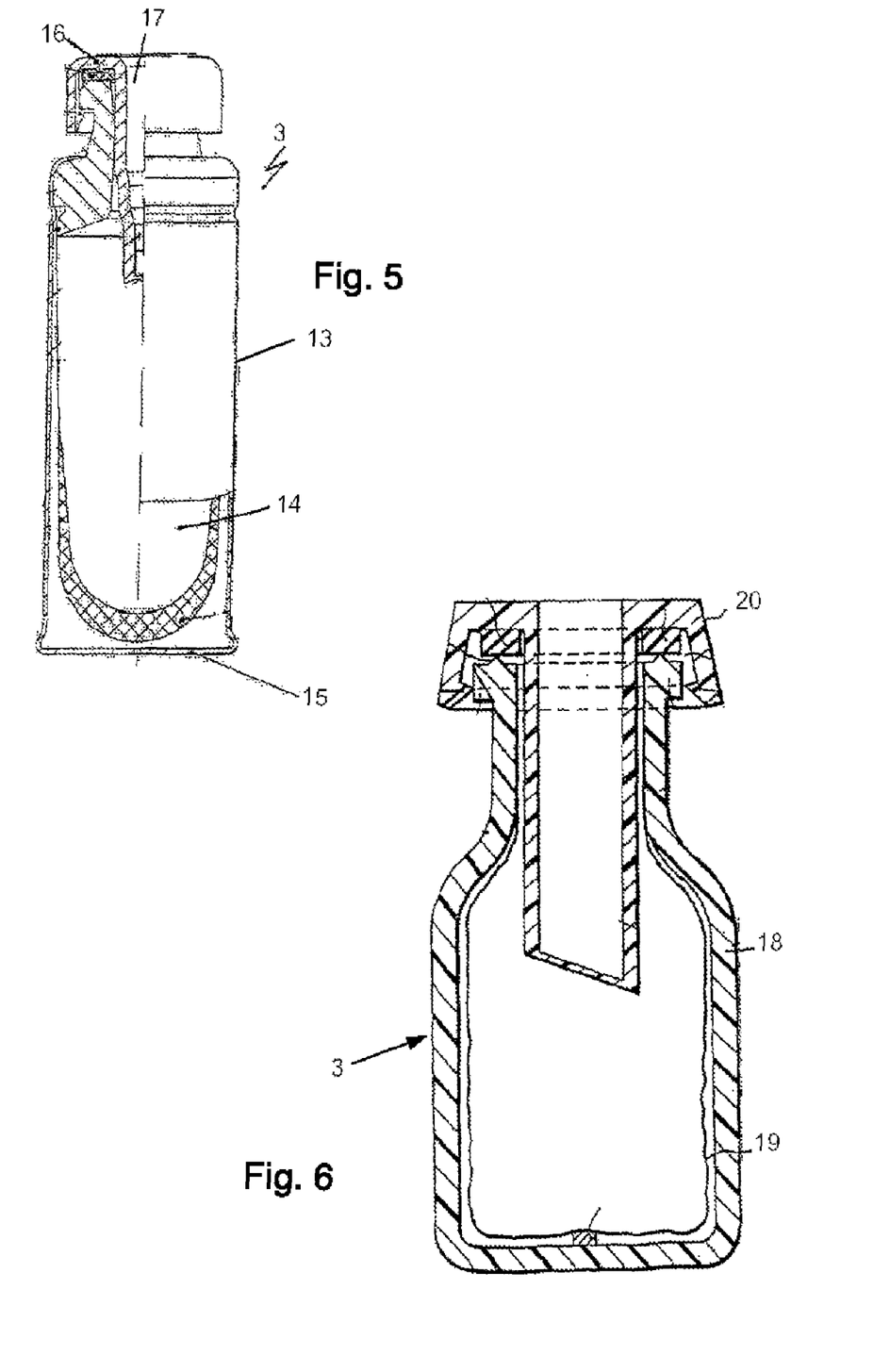
FIG. 5 shows a bottle-shaped container for use in the method according to the invention.
FIG. 6 shows a container designed as a collapsible bag for use in the method according to the invention.

A further container 3 for use in the method of the invention is formed as a closed double-layer, bottle-shaped container, as an inhaler cartridge 13, and consists of a bag 14 of a metal film and/or plastics film, which is inserted into a sleeve 15 of metal or plastics. The bag 14 comprises a tightly closed flange 16 with a guide channel 17 for a cannula. A press fit or seal is furthermore provided, which seals a cannula that penetrates the guide channel 17 and opens the latter. The cannula may be that of an inhaler, from which a small amount of the liquid can be removed from the container 3. Such a container 3 is also described in detail in WO 99/43571.

A further container 3 suitable for use in the method of the invention serves as a cartridge for an inhaler described in WO 91/14468 and WO 97/12687, and is formed as a double-layer bottle-shaped container with a rigid outer sleeve 18 and an inner container 19 connected in a punctiform manner to the outer sleeve 18, the inner container being able to collapse relative to the outer sleeve. The container is closed with a cap 20. Such containers are described in detail for example in EP 532 873 and WO 96/06011.

The invention claimed is:

1. A method for measuring the permeability rate of a closed container with respect to a liquid, wherein the container is suitable for accommodating a pharmaceutical active constituent formulation, the method comprising the steps of: a) filling the container with the liquid, b) charging the container with a gas, and c) analyzing the increase in the amount of the liquid in the gas.

2. A method according to claim 1, characterised in that water is used as the liquid.

3. A method according to claim 1, characterised in that the clay is soaked in water and is introduced into the container in such a way that it completely fills the container.

4. A method according to claim 1, characterised in that nitrogen is used as the gas.

5. A method according to claim 1, characterised in that the gas is dried before the container is charged.

6. A method according to claim 1, characterised in that an evaluation unit that comprises quartz resonators is used for analysing the gas.

7. A method according to claim 1, characterised in that the liquid is absorbed by a porous solid body that matches the size and shape of the container.

8. A method according to claim 7, characterised in that the solid body is made from clay.

9. A method according to claim 1, characterised in that the container is introduced into a closed test chamber through which the gas flows.

10. A method according to claim 9, characterised in that the test chamber is climatically controlled.

11. A method according to claim 9, characterised in that seals of the test chamber are dried beforehand.

12. A method according to claim 9, characterised in that the gas flows through the test chamber at a constant mass flow rate and at a constant pressure.

13. A method according to claim 9, characterised in that the container is dried before it is placed in the test chamber.

14. A method according to claim 9, characterised in that the test chamber is introduced into a closed chamber.

15. A container for use in the method according to claim 1, characterised in that the container is a blister.

16. A container according to claim 15, characterised in that the blister (4) consists of at least one cover film and at least one cup for the carrier film containing the active constituent formulation, wherein the cover film and the carrier film are tightly joined to one another to seal the cup hermetically.

17. A container according to claim 16, characterised in that the cover film is connected to the carrier film by means of a hot sealing lacquer.

18. A container according to claim 16, characterised in that the cover film and/or the carrier film are formed as a metal and/or plastics and/or paper film.

19. A container for use in the method according to claim 1, characterised in that the container (3) is a closed double-layer, bottle-shaped container (3) with a rigid outer sleeve (18) and an inner container (19) mechanically connected to the outer sleeve (18) in a punctiform manner, which inner container can collapse relative to the outer sleeve (18).

20. A container according to claim 19, characterised in that the container (3) is produced by means of a co-extrusion process.

21. A container according to claim 19, characterised in that the outer sleeve (18) consists of polypropylene, and the inner container (19) consists of polyethylene.

22. A container according to claim 19, characterised in that the container (3) is opened by inserting a cannula through a cap (20) or by inserting a cannula through the flange (16).

23. A container for use in the method according to claim 1, characterised in that the container (3) is a closed collapsible bag (14) provided with a flange (16).

24. A container according to claim 23, characterised in that the bag (14) consists of a metal film, for example an aluminium film, and/or a plastics film or a metal film coated with a plastics.

25. A container according to claim 23, characterised in that the bag (14) is embedded in a rigid sleeve (15).

* * * * *